United States Patent

Goble et al.

[11] Patent Number: 5,860,975
[45] Date of Patent: Jan. 19, 1999

[54] ELECTROSURGICAL INSTRUMENT

[75] Inventors: Nigel Mark Goble, Nr. Cardiff; Colin Charles Owen Goble, South Glamorgan, both of Wales

[73] Assignee: Gyrus Medical Limited, Cardiff, Wales

[21] Appl. No.: 573,187

[22] Filed: Dec. 15, 1995

[30] Foreign Application Priority Data

Dec. 21, 1994 [GB] United Kingdom ............. 9425781

[51] Int. Cl.$^6$ .................................................. A61B 17/36
[52] U.S. Cl. ............................. 606/45; 606/41; 606/48
[58] Field of Search ...................... 606/41, 42, 45–52

[56] References Cited

U.S. PATENT DOCUMENTS

| | | | |
|---|---|---|---|
| 5,324,289 | 6/1994 | Eggers | 606/48 |
| 5,352,222 | 10/1994 | Rydell | 606/52 |
| 5,484,436 | 1/1996 | Eggers et al. | 606/48 |
| 5,540,685 | 7/1996 | Parins et al. | 606/51 |
| 5,573,534 | 11/1996 | Stone | 606/48 |
| 5,603,711 | 2/1997 | Parins et al. | 606/51 |

FOREIGN PATENT DOCUMENTS 2680314   8/1991   France ........................ 606/51

*Primary Examiner*—Michael Peffley

[57] ABSTRACT

An electrosurgical cutting device comprises an instrument body, and first and second cutting blades, at least one of which is pivotally mounted on the body to execute a scissor action with respect to the other blade. Electrical supply conductors associated with the body supply an electrosurgical voltage to the first and second blades. The first blade is a composite blade comprising a conductive outer electrode, an inner conductive layer, sandwiched between the outer electrode and the inner layer, an insulating layer. The supply conductors are connected respectively to the outer electrode and to the inner layer.

16 Claims, 2 Drawing Sheets

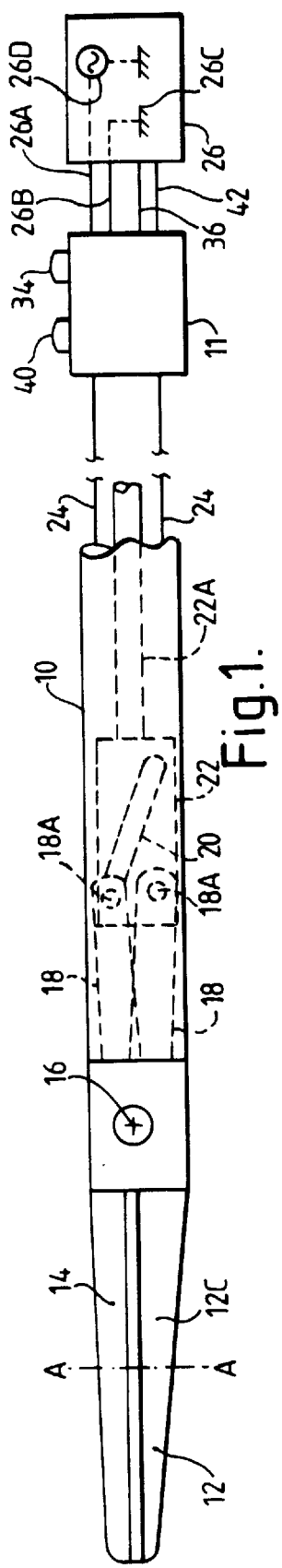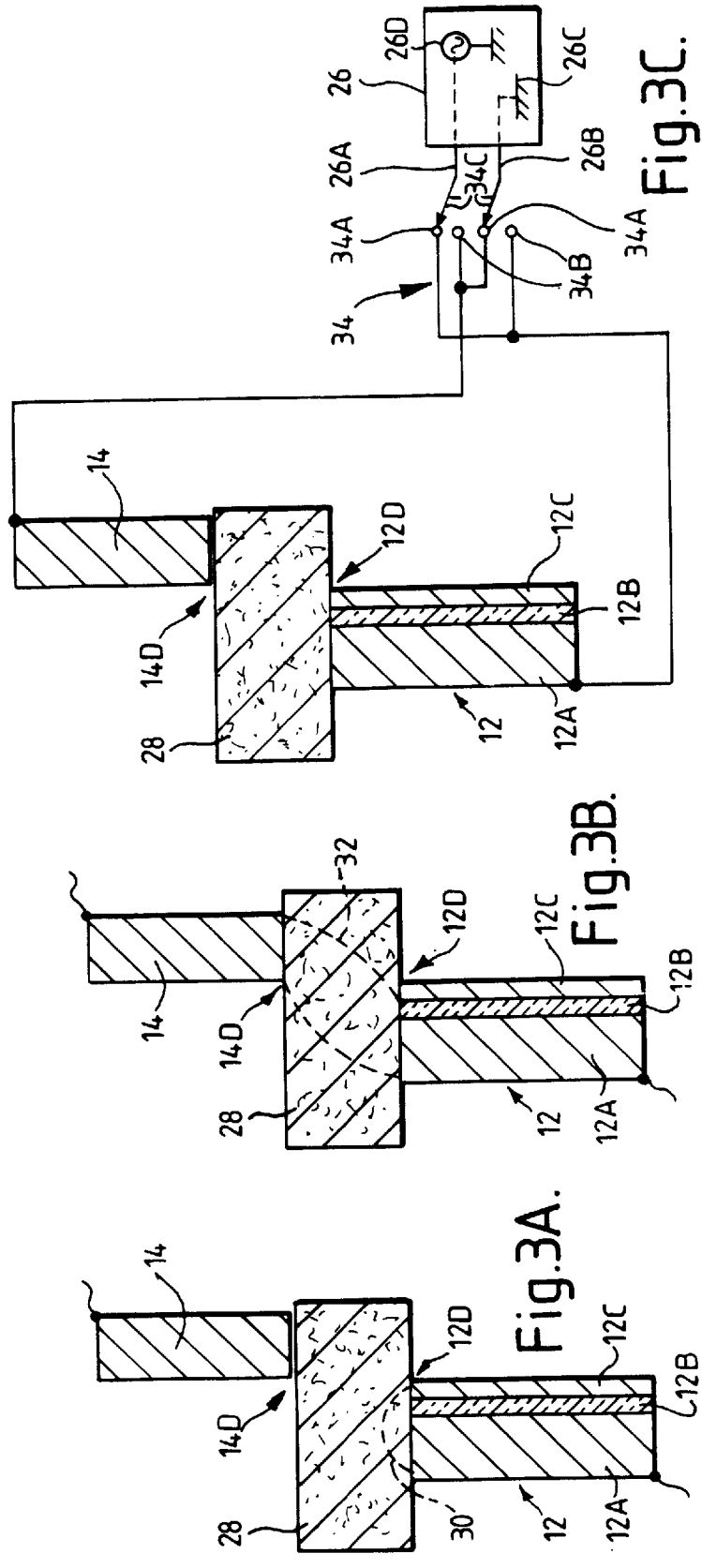

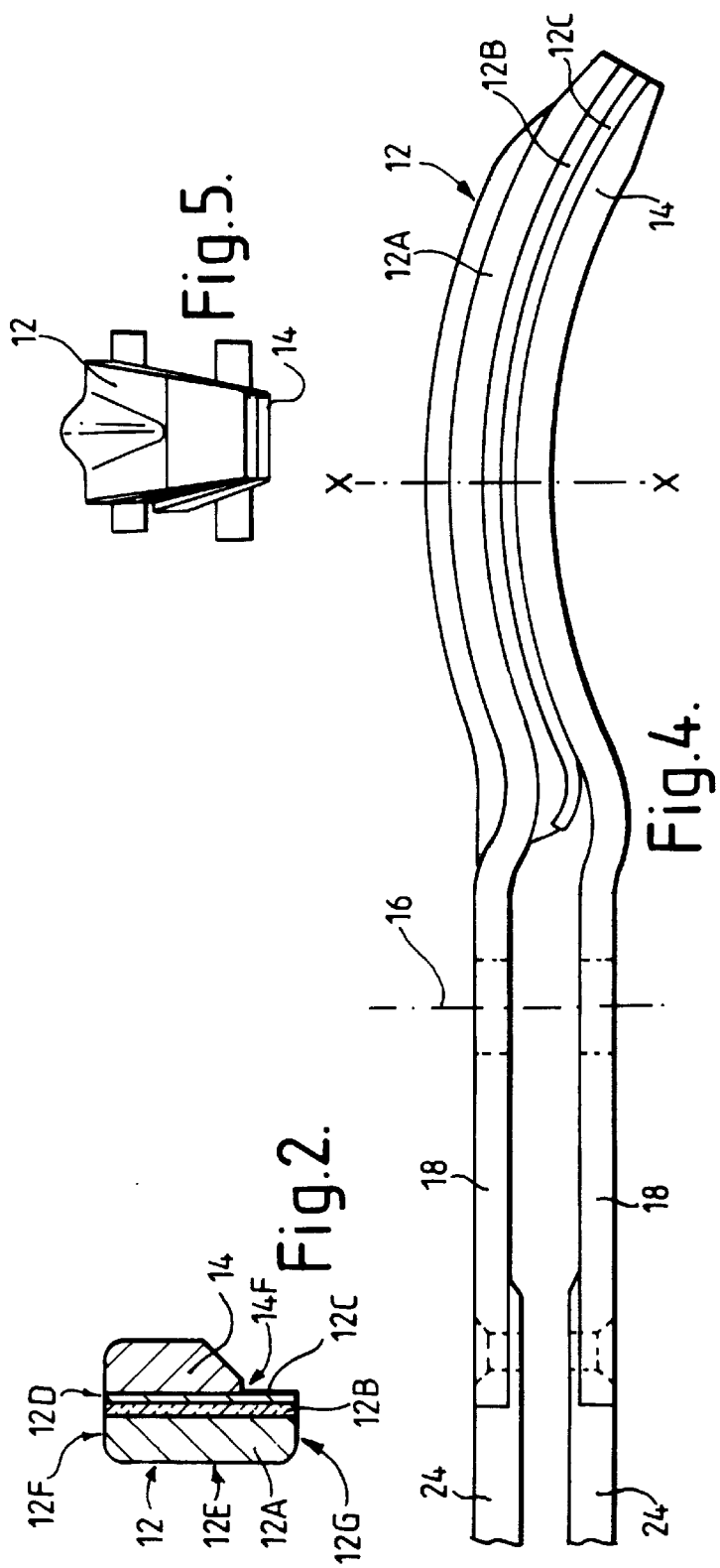

ELECTROSURGICAL INSTRUMENT

BACKGROUND OF THE INVENTION

This invention relates to an electrosurgical cutting device having a pair of blades which are mounted so as to execute a scissor action whereby, when an electrosurgical voltage is applied, the device acts simultaneously to desiccate and shear living tissue.

It is known to perform surgical cutting using a scissor instrument having a pair of blades mounted at the end of an elongate shaft, each blade being rotatable about an axis which is transverse to the shaft in response to movement of a control rod extending between the blades and a handpiece at the other end of the shaft. The two blades are electrically insulated from each other and have ceramic coatings on their opposing surfaces so that they can be connected to a source of bipolar electrosurgical power without electrical short-circuiting. Tissue trapped between the blades is subjected to passage of electrosurgical current distally of the intersection of the cutting edges of the blades so as to desiccate the tissue prior to mechanical parting as the blades are closed together.

SUMMARY OF THE INVENTION

According to the present invention, there is provided an electrosurgical cutting device comprising an instrument body, first and second cutting blades at least one of which is pivotally mounted on the body to execute a scissor action with respect to the other blade, and electrical supply conductors associated with the body for supplying a bipolar electrosurgical voltage to the first and second blades, wherein the first blade is a composite blade comprising a conductive outer electrode, an inner conductive layer and, sandwiched between the outer electrode and the inner layer, an insulating layer, the supply conductors being connected respectively to the outer electrode and to the inner layer. Advantageously, one of the supply conductors is connected directly to the inner layer.

Conveniently, one of the supply conductors is coupled to the second blade and is electrically connected to the inner layer of the composite first blade by electrical contact between the second blade and the inner layer. Preferably, the second blade has a conductive body which is in electrical contact with the inner layer of the composite first blade, and said one supply conductor is connected to the conductive body so that the conductive body is electrically connected in series between said one supplyconductor and the inner layer.

Each blade may have a cutting edge which is so oriented that the blades execute a progressive shearing action, each cutting edge being formed of a metallic material. Indeed, the second blade preferably is a simple metallic blade having an entirely metallic body, with the cutting edge formed on the body. In a preferred embodiment, both blades are pivotally mounted on the instrument body.

If the blades are considered to have shearing surfaces which, during the cutting action, progressively overly one another in a face-to-face interengaging relationship, and both shearing surfaces are on conductive parts of the respective blades, the inner layer of the composite first blade and at least that part of the second blade supporting its shearing surface are at one electrical potential. The outer electrode of the composite first blade is at a different electrical potential, thereby producing an electric field both (a) between the outer electrode and the inner conductive layer of the composite first blade and (b) between the outer electrode of the composite first blade and the second blade due to the electrical contact between the shearing surfaces.

Each blade preferably comprises an elongate member having an outer surface, an inner shearing surface, and a cutting edge running along the blade and defining a boundary between the shearing surface and the outer surface along one side of the shearing surface, the blades being so mounted on the instrument body that their respective cutting edges execute a progressive shearing action as the blades are moved to a closed configuration with the shearing surfaces in a face-to-face relationship, the outer surface of the composite first blade defining a cutting face running along the blade adjacent to its cutting edge, each of the inner conductor layer, the insulating layer, and the outer electrode being exposed along the cutting face, with the shearing surface being formed, at least adjacent the cutting edge, on the inner conductive layer.

Preferably, the second blade has a conductive body and also has a cutting face running along the blade adjacent to its cutting edge, the conductive body being exposed at least at the cutting edge and over the area of the cutting face. The cutting faces of the blades are preferably, at least in part, generally perpendicular to the shearing surfaces so that distally of the intersection of the cutting edges, the cutting faces face each other, albeit in an offset relationship so that they make electrical contact with a piece of tissue extending transversely between the blades. Consequently, in use of the device, tissue located between the blades and distally of the intersection of the cutting edges is subjected to electrosurgical currents flowing through the tissue, on the one hand, between the outer electrode of the composite blade and the inner layer of that blade and, on the other hand, between the composite blade outer electrode and the second blade. This produces desiccation prior to mechanical division at the intersection of the cutting edges as the blades are moved towards their closed configuration.

In some circumstances, particularly when the orientation of the tissue plane makes mechanical division difficult, the preferred embodiment of the invention can be used for pure electrosurgical cutting, i.e. without mechanical division. To achieve this, the outer electrode, the insulating layer, and the inner conductive layer of the composite first blade of the preferred embodiment are each exposed along an electrosurgical cutting surface which forms part of the outer surface of the composite first blade running along that blade adjacent to the opposite side of the shearing surface of that blade from the cutting edge. The second blade is made generally narrower than the composite first blade, and is so mounted that, in the closed configuration of the blades, the cutting edge of the second blade runs along the shearing surface of the composite first blade spaced back from the electrosurgical cutting surface of the composite first blade. Consequently, on the opposite side of the composite first blade from its cutting edge, the outer electrode, the insulating layer, and the inner conductive layer present a strip surface along which all three are exposed side-by-side so that, when the blades are in their closed configuration, this side of the composite first blade can be used in the manner of a knife when an electrosurgical voltage is applied across the insulating layer.

The invention also provides electrosurgical cutting apparatus including an electrosurgical generator and a bipolar electrosurgical cutting device as described above, the generator having an unbalanced output with an active terminal and a passive terminal, wherein the supply conductor connections are so arranged that for tissue desiccation and mechanical cutting, the active terminal is connected to the outer electrode of the composite first blade. Similarly, for electrosurgical cutting, the active terminal is preferably connected to the second blade or the inner layer of the composite first blade.

It is possible to incorporate a control switch in the cutting device, so that the supply conductor connections may be reversed according to whether the device is being used for combined tissue desiccation and mechanical cutting, or for electrosurgical cutting.

BRIEF DESCRIPTION OF THE DRAWINGS

The invention will now be described, by way of example, with reference to the drawings, in which:

FIG. 1 is a diagram of electrosurgical apparatus including, in plan view, part of a bipolar electrosurgical cutting instrument constructed in accordance with the invention, showing a pair of cutting blades pivotally mounted on the end of an elongate instrument body, the diagram showing other elements of the apparatus in block form;

FIG. 2 is a cross-section through the blades taken on the line A–A in FIG. 1;

FIGS. 3A and 3B are diagrammatic cross-sections of the blades when in use, showing the distribution of electrosurgical current in a piece of living tissue between the blades;

FIG. 3C is a diagrammatic cross-section of the blades together with an associated electrosurgical generator and switch;

FIG. 4 is a side elevation of the blades of a second electrosurgical instrument constructed in accordance with the invention;

FIG. 5 is an end view of the blades of FIG. 4; and

FIG. 6 is a cross-section taken on the line X—X in FIG. 4.

DETAILED DESCRIPTION OF THE DRAWINGS

Referring to FIGS. 1 and 2 of the drawings, a first electrosurgical cutting instrument constructed in accordance with the invention, intended for laparoscopic use, has an elongate tubular body 10 which is attached at its proximal end to a handpiece 11 (shown in diagrammatic block form) in a conventional manner. At the distal end of the body 10 are two cutting blades 12 and 14, each pivotally mounted for rotation about an axis 16 oriented transversely of the axis of the body 10. Each blade 12 and 14 has a finger part 18 extending proximally beyond the axis 16, the finger parts bearing pins 18A which locate in grooves 20 (only one of which is shown in FIG. 1) on opposite sides of a reciprocable actuator 22 inside the body 10. A control rod 22A connects the actuator 22 to a trigger mechanism (not shown) in the handpiece 11 so that, when the trigger mechanism is operated, the actuator moves longitudinally within the body 10, causing the blades 12 and 14 to pivot about the transverse axis 16. Electrical supply conductors 24 pass through the tubular body 10 between the handpiece 11 and their connections with the respective blades 12 and 14.

The handpiece 11 is connected to an electrosurgical generator 26.

As will be seen from FIG. 2, the blade 12 is a composite blade comprising a metallic outer electrode 12A, an insulating layer 12B, and an inner conductive layer 12C. The other blade 14 is a simple blade having a metallic body and, in this embodiment, is narrower than the composite blade 12 in terms of the width of the shearing surface. The inner conductive layer 12C of the composite blade 12 forms the shearing surface of that blade, which shearing surface is terminated on one side by a cutting edge 12D. The outer surface 12E of the composite blade 12 extends from the cutting edge 12D around to the other side of the shearing surface formed by the layer 12C. The portion 12F of the outer surface 12E which lies alongside the cutting edge 12D may be regarded as a cutting face, the outer electrode 12A being exposed at least at this cutting face 12F. The insulating layer 12B and the inner conductive layer 12C are also exposed along the face 12F.

The simple blade 14 also has a shearing surface which, when the blades 12 and 14 are in their closed configuration as shown in FIGS. 1 and 2, faces the shearing surface of the composite blade 12, and it also has a cutting face 14F which, when the blades are in their open configuration, faces the cutting face 12F of the composite blade 12, albeit in an offset relationship. The cutting face 14F of the simple blade 14 terminates in a cutting edge 14D which overlies the shearing surface formed by the inner layer 12C of the composite blade 12 when the blades are in the closed configuration.

The supply conductors 24 are connected respectively to the outer electrode 12E of the composite blade 12, and to the simple blade 14. Thus, when an electrosurgical power source, such as the generator 26, is applied at the handpiece end of the conductors 24, an electrosurgical voltage is developed between, on the one hand, the outer electrode 12A and the inner layer 12C and, on the other hand, between the outer electrode 12A and the simple blade 14.

The effect of this method of connection is illustrated in FIGS. 3A and 3B. Referring to these figures, the blades 12 and 14 are here shown in an open configuration with a piece of living tissue 28 trapped in a transverse orientation between the blades distally of the intersection of their cutting edges 12D and 14D. There are two current paths 30 and 32 through the tissue 28, the first path 30 being between the outer electrode 12A and the inner conductive layer 12C of the composite blade 12, as shown in FIG. 3A. It will be noted here that the inner conductive layer 12C is at the same potential as the simple blade 14 due to electrical contact between the shearing surfaces and/or the cutting edges 12D and 14D of the two blades proximally of the cutting edge intersection point. The second current path 32 extends between the outer electrode 12A of the composite blade 12, and the cutting edge 14D of the simple blade 14, as shown in FIG. 3B. In practice, the two current paths 30 and 32 combine, producing a desiccating action along a line in the tissue 28 corresponding to the line of the mechanical parting which occurs when the blades 12 and 14 are moved from their open to their closed configuration, thereby preventing haemorrhaging along the line of cut.

Since there is no flow of electrosurgical current between the inner conductive layer 12C of the composite blade 12, and the simple blade 14, there is no need for insulating material at the shearing surfaces.

The current path 30 provides a small area of desiccation compared to the principal pathway 32 shown in FIG. 3B, the overall effect being a summation of the currents through both pathways. Both pathways 30 and 32 are elongated in the direction of the blades 12 and 14. It should also be noted that, as the blades 12 and 14 are closed, the tissue 28 will become compressed, and the amount of tissue desiccated increases.

As will be appreciated from FIGS. 3A and 3B, rotating the instrument clockwise as viewed in these figures will increase the contact between the tissue 28 and both the blades 12 and 14, thereby reducing the tissue contact impedance, the outer electrode 12A and the simple blade 14 both having conductive outer surfaces over the relevant tissue-contacting parts.

It will also be appreciated that, since there is no insulating layer on the shearing surface of the simple blade 14, this may be contacted to the tissue 28 when the scissors are in an open configuration, with the bipolar electrosurgical circuit being completed by the outer surface 12E, 12F of the composite blade 12. Accordingly, a comparatively large volume of tissue 28 is contained within the current path leading to a broad desiccation region prior to mechanical division.

Referring again to FIG. 2, it will be seen that the outer electrode 12A, the insulating layer 12B, and the inner conductive layer 12C are all exposed along a surface strip 12G forming part of the outer surface 12E of the composite blade 12, which surface strip is opposite to the cutting face 12F. This surface strip 12G can be used as an electrosurgical knife. It will be noted that the simple blade 14 is narrower than the composite blade 12, and that when the blades are in their fully closed configuration, the cutting face 14F of the simple blade 14 runs along the shearing surface of the composite blade 12 spaced from the surface strip 12G, so as to be clear of the electrosurgical cutting edge.

The effectiveness of electrosurgical cutting using the electrosurgical cutting edge 12G can be enhanced by increasing the current density in the tissue adjacent to the cutting edge 12D. In the case of an electrosurgical generator 26 having an unbalanced output, this can be achieved by connecting an "active" or "feed" output terminal 26A of the generator to the simple blade 14 (or directly to the inner layer 12C of the composite blade 12), and a "passive" or "return" output terminal 26B to the outer electrode 12A of the composite blade 12. The effect of such connections is as follows. Since the passive output terminal 26B of the generator 26 is coupled, at least for alternating currents, to an internal ground rail 26C of the generator 26, while the active terminal 26A is connected to an oscillator or amplifier output 26D, the leakage current through the patient to earth is greater from the active terminal 26A than from the passive terminal 26B, the capacitance from the terminal 26B to earth being the greater. As a result, not all of the current applied to the patient tissue from the active terminal 26A is returned via the terminal 26B. Some of it is capacitively coupled to earth. By connecting the active terminal 26A effectively to the inner layer 12C, the peak current density at the interface between the tissue 28 and the electrosurgical cutting face 12G is maximised because the surface area of the layer 12C at the cutting face is smaller than the surface area of the outer electrode 12A.

In contrast to the requirements for electrosurgical cutting, the preferred current distribution for desiccation is as near uniform as possible across the interface between the tissue and the composite blade 12. Accordingly, for combined desiccation and mechanical cutting (as shown in FIGS. 3A and 3B), it is preferred that the active terminal 26A is connected to the outer electrode 12A of the composite blade 12, while the passive terminal 26B is connected to the simple blade 14 (and effectively the inner layer 12C). It is, therefore, of advantage to provide a switch 34 for reversing the connections of supply conductors 24 to the terminals 26A and 26B respectively, according to whether desiccation or electrosurgical cutting is required. This switch 34 is shown in greater detail in FIG. 3C, the switch having two pairs of contacts 34A and 34B and a double-armed contact 34C. The double-armed contact 34C can be moved from a first operating position (shown in FIG. 3C), in which the active terminal 26A is connected to the outer electrode 12A and the passive terminal 26B is connected to the simple blade 14, and the instrument is used for desiccation, to a second operating position, in which the active terminal 26A is connected to the simple blade 14 and the passive terminal 26B is connected to the electrode 12A, and the instrument is used for electrosurgical cutting.

The change-over switch 34 may be provided on the handpiece 11 as shown in FIG. 1, the actual switching contacts 34A, 34B and 34C preferably being located in the generator 26, with the contacts being operated by relays controlled from the switch 34 by means of a control wire 36. The handpiece 11 also includes an on/off switch 40 for controlling the application of electrosurgical power to the conductors 24. Again, actual switching for this function may be performed by a relay controlled via a control wire 42 between switch 40 and the generator 26.

Referring next to FIGS. 4 to 6, a second electrosurgical instrument constructed in accordance with the invention has curved cutting blades 12 and 14, the blades being curved about an axis of curvature which is spaced from, and transverse to, the longitudinal axis of the device. The composite blade 12, as in the first embodiment, has an outer electrode 12A, an inner insulating layer 12B made from an epoxy resin adhesive, and an inner conductive layer 12C formed of a hard wear-resistant metal. The other blade 14 is curved to match the curvature of the composite blade 12, as shown. As before, this is a simple metallic component. Both blades 12 and 14 are rotatable about a transverse pivot axis 16, and have finger parts 18 extending proximally from the axis 16 for engaging an actuator (not shown, but similar to the actuator 22 shown in FIG. 1). FIG. 4 shows the attachment of electrosurgical supply conductors 24 to the finger portions 18 of the blades 12 and 14. Referring to FIG. 6 in particular, it will be seen that the composite blade 12 is formed with an outer rib 12H for additional strength.

We claim:

1. An electrosurgical cutting device comprising an instrument body, first and second cutting blades at least one of which is pivotally mounted on the body to execute a scissor action with respect to the other blade, and electrical supply conductors associated with the body for supplying an electrosurgical voltage to the first and second blades, wherein the first blade is a composite blade comprising a conductive outer electrode, an inner conductive layer and, sandwiched between the outer electrode and the inner layer, an insulating layer, the supply conductors being connected respectively to the outer electrode and to the inner layer.

2. A device according to claim 1, wherein one of the supply conductors is connected directly to the inner layer.

3. A device according to claim 1, wherein one of the supply conductors is coupled to the second blade and is electrically connected to the inner layer of the composite first blade by electrical contact between the second blade and the inner layer.

4. A device according to claim 3, wherein the second blade has a conductive body which is in electrical contact with the inner layer of the composite first blade, and wherein said one supply conductor is connected to the conductive body so that the conductive body is electrically connected in series between said one supply conductor and the inner layer.

5. A device according to claim 1, wherein each blade has a cutting edge which is so oriented that the blades can execute a progressive shearing action, each cutting edge being formed of a metallic material.

6. A device according to claim 1, wherein the second blade has an entirely metallic body and its cutting edge is formed on the metallic body.

7. A device according to claim 1, wherein both blades are pivotally mounted on the instrument body.

8. A device according to claim 1, wherein each blade comprises an elongate member having an outer surface, an inner shearing surface, and a cutting edge running along the blade and defining a boundary between the shearing surface and the outer surface along one side of the shearing surface, wherein the blades are so mounted on the instrument body that their respective cutting edges execute a progressive shearing action as the blades are moved to a closed configuration with the shearing surfaces in a face-to-face relationship, wherein the outer surface of the composite first blade defines a cutting face running along the blade adjacent to its cutting edge, each of the inner conductive layer, the insulating layer and the outer electrode being exposed along the cutting face with the shearing surface being formed, at least adjacent to the cutting edge, on the inner conductive layer.

9. A device according to claim 8, wherein the second blade has a conductive body and also has a cutting face running along the blade adjacent to its cutting edge, the conductive body being exposed at least at the cutting edge and along the cutting face.

10. A device according to claim 9, wherein the conductive body of the second blade is exposed over at least a major part of the shearing surface of that blade.

11. A device according to claim 8, wherein the outer electrode, the insulating layer and the inner conductive layer of the composite first blade are each exposed along an electrosurgical cutting surface which forms part of said outer surface of the composite first blade running along that blade adjacent to the shearing surface of that blade.

12. A device according to claim 11, wherein the electrosurgical cutting surface extends along the composite first blade adjacent to the opposite side of the shearing surface of that blade from the cutting edge, and wherein the blades are so shaped and mounted that, in their closed configuration, the cutting edge of the second blade runs along the shearing surface of the composite first blade and is spaced from the composite first blade electrosurgical cutting surface.

13. A device according to claim 1, further comprising a switch mounted on the instrument body and electrically connected to the supply conductors for reversing the polarity of the supply conductors.

14. Electrosurgical cutting apparatus including an electrosurgical generator and a bipolar electrosurgical cutting device, the bipolar electrosurgical device comprising an instrument body, first and second cutting blades at least one of which is pivotally mounted on the body to execute a scissor action with respect to the other blade, and electrical supply conductors associated with the body for supplying an electrosurgical voltage to the first and second blades, wherein the first blade is a composite blade comprising a conductive outer electrode, an inner conductive layer and, sandwiched between the outer electrode and the inner layer, an insulating layer, the supply conductors being connected respectively to the outer electrode and to the inner layer, the generator having an unbalanced output with an active terminal and a passive terminal, wherein the supply conductor connections are so arranged that for tissue desiccation and mechanical cutting the active terminal is connected to the outer electrode of the composite first blade.

15. Electrosurgical apparatus including an electrosurgical generator and a bipolar electrosurgical cutting device, the bipolar electrosurgical cutting device comprising an instrument body, first and second cutting blades at least one of which is pivotally mounted on the body to execute a scissor action with respect to the other blade, and electrical supply conductors associated with the body for supplying an electrosurgical voltage to the first and second blades, wherein the first blade is a composite blade comprising a conductive outer electrode, an inner conductive layer and, sandwiched between the outer electrode and the inner layer, an insulating layer, the supply conductors being connected respectively to the outer electrode and to the inner layer, the generator having an unbalanced output with an active terminal and a passive terminal, wherein the supply conductor connections are so arranged that for electrosurgical cutting the passive terminal is connected to the outer electrode of the composite first blade.

16. Apparatus according to claim 15, wherein the cutting device includes a switch mounted on the instrument body for reversing the polarity of the generator terminals to the blades.

\* \* \* \* \*